US011596648B2

(12) United States Patent
Kessler et al.

(10) Patent No.: US 11,596,648 B2
(45) Date of Patent: Mar. 7, 2023

(54) EMOLLIENT TOPICAL DISINFECTANTS

(71) Applicant: I2Pure Corp., Reston, VA (US)

(72) Inventors: Jack Kessler, Southborough, MA (US); David C. Litzinger, Poway, CA (US); Christopher Rhodes, San Diego, CA (US); Andrew M. Cerro, Alisa Viejo, CA (US)

(73) Assignee: I2PURE CORP., Reston, VA (US)

( * ) Notice: Subject to any disclaimer, the term of this patent is extended or adjusted under 35 U.S.C. 154(b) by 0 days.

(21) Appl. No.: 16/088,992

(22) PCT Filed: Jul. 19, 2017

(86) PCT No.: PCT/US2017/042726
§ 371 (c)(1),
(2) Date: Sep. 27, 2018

(87) PCT Pub. No.: WO2018/017645
PCT Pub. Date: Jan. 25, 2018

(65) Prior Publication Data
US 2019/0381093 A1 Dec. 19, 2019

Related U.S. Application Data

(60) Provisional application No. 62/365,035, filed on Jul. 21, 2016.

(51) Int. Cl.
A61K 33/18 (2006.01)
A61P 31/04 (2006.01)
A61K 9/00 (2006.01)
A61K 9/06 (2006.01)
A61K 47/10 (2017.01)

(52) U.S. Cl.
CPC ............ A61K 33/18 (2013.01); A61K 9/008 (2013.01); A61K 9/0043 (2013.01); A61K 9/06 (2013.01); A61K 47/10 (2013.01); A61P 31/04 (2018.01)

(58) Field of Classification Search
CPC ...... A61K 33/18; A61K 9/0043; A61K 9/008; A61K 9/06; A61K 47/10; A61K 9/0014; A61K 47/32; A61K 47/40; A61K 9/0073; A61K 47/36; A61P 31/04; A61P 31/00; Y02A 50/30
See application file for complete search history.

(56) References Cited

U.S. PATENT DOCUMENTS

| | | |
|---|---|---|
| 1,896,171 A | 2/1933 | Harry |
| 2,550,622 A | 4/1951 | Clayton |
| 3,279,981 A | 10/1966 | Geiger et al. |
| 4,937,072 A | 6/1990 | Kessler et al. |
| 4,954,351 A | 9/1990 | Sackler et al. |
| 5,013,859 A | 5/1991 | Globus |
| 5,227,161 A | 7/1993 | Kessler |
| 5,370,815 A | 12/1994 | Kessler |
| 5,629,024 A | 5/1997 | Kessler et al. |
| 5,639,481 A | 6/1997 | Kessler et al. |
| 5,648,075 A | 7/1997 | Kessler et al. |
| 5,849,291 A | 12/1998 | Kessler |
| 5,885,592 A | 3/1999 | Duan et al. |
| 5,897,872 A | 4/1999 | Picciano |
| 5,922,314 A | 7/1999 | Hoang et al. |
| 5,962,029 A | 10/1999 | Duan et al. |
| 6,015,836 A | 1/2000 | Martin |
| RE36,605 E | 3/2000 | Kessler |
| 6,228,354 B1 | 5/2001 | Jeng |
| 6,248,335 B1 | 6/2001 | Duan et al. |
| 6,261,577 B1 | 7/2001 | Kessler |
| 6,432,426 B2 | 8/2002 | Kessler |
| 7,147,873 B2 | 12/2006 | Scholz et al. |
| 8,303,994 B2 | 11/2012 | Kessler et al. |
| 8,691,290 B2 | 4/2014 | Kessler et al. |
| 8,808,722 B2 | 8/2014 | Scholz et al. |
| 8,840,932 B2 | 9/2014 | Scholz et al. |
| 9,114,156 B2 | 8/2015 | Childers |
| 2001/0005612 A1 | 12/2001 | Kessler |
| 2003/0026852 A1 | 2/2003 | Duan et al. |
| 2004/0091553 A1 | 5/2004 | Foret |
| 2005/0023300 A1 | 10/2005 | Gradle et al. |
| 2005/0233006 A1 | 10/2005 | Gradle et al. |
| 2006/0177511 A1 | 8/2006 | Scholz et al. |
| 2006/0280809 A1 | 12/2006 | Leshchiner et al. |
| 2009/0017139 A1 | 1/2009 | Kessler |
| 2015/0118688 A1 | 4/2015 | Weidemaier et al. |
| 2015/0147400 A1 | 5/2015 | Kessler et al. |
| 2017/0208814 A1 | 7/2017 | Kolsky et al. |

(Continued)

FOREIGN PATENT DOCUMENTS

| | | |
|---|---|---|
| JP | S51144738 A | 12/1976 |
| JP | S60185720 A | 9/1985 |

(Continued)

OTHER PUBLICATIONS

International Search Report and Written Opinion dated Oct. 30, 2017, 12 pages.
Duan Y, et. al., "Properties of an enzyme-based low-level iodine disinfectant," J Hosp Infect. Nov. 1999; 43(3):219-29.
EPO, Extended European Search Report for Application No. 17831741.8, dated May 20, 2020.
Favero, "Iodine—Champagne in a Tin Cup," Infection Control and Hospital Epidemiology. Jan.-Feb. 1982; 3(1):30-2.
Hickey et. al., "Control of the Amount of Free Molecular Iodine in Iodine Germicides," J Pharm Pharmacol. Dec. 1997; 49(12): 1195-9.

(Continued)

Primary Examiner — Aradhana Sasan
(74) Attorney, Agent, or Firm — Perkins Coie LLP; Yingli Wang

(57) ABSTRACT

This invention relates generally to an emollient topical composition of matter that contains molecular iodine with a reduced effective vapor pressure. In specific embodiments, the composition reduces the loss of molecular iodine to the atmosphere under storage conditions after application to mammalian tissue.

14 Claims, 11 Drawing Sheets

(56) References Cited

U.S. PATENT DOCUMENTS

| | | | |
|---|---|---|---|
| 2018/0136204 A1 | 5/2018 | Weidemaier et al. |
| 2018/0296594 A1 | 10/2018 | Kessler et al. |
| 2018/0360048 A1 | 12/2018 | Kolsky et al. |
| 2019/0105344 A1 | 4/2019 | Kessler |
| 2020/0129543 A1 | 4/2020 | Loscher |

FOREIGN PATENT DOCUMENTS

| | | | |
|---|---|---|---|
| JP | H08310959 A | 11/1996 |
| JP | 2005289866 A | 10/2005 |
| JP | 2005306764 A | 11/2005 |
| JP | 2009039525 A | 2/2009 |
| WO | 2012002943 A1 | 1/2012 |
| WO | 2012135055 A2 | 10/2012 |
| WO | 2012177251 A1 | 12/2012 |
| WO | 2015-153258 | 10/2015 |
| WO | 2022036280 A1 | 2/2022 |

OTHER PUBLICATIONS

Nava-Villalba et al, "6-Iodolactone, key mediator of antitumoral properties of iodine," Prostaglandins & other Lipid Mediators. 2014; vol. 112, pp. 27-33.

CNIPA, First Office Action for Chinese Patent Application No. 201780054315.6. dated Feb. 23, 2021. 11 pages with English translation.

Gottardi, W. "The uptake and release of molecular iodine by the skin: chemical and bactericidal evidence of residual effects caused by povidone-iodine preparations" Journal of Hospital Infection, 1995, vol. 29, pp. 9-18.

JPO, Notice of Reasons for Refusal for Japanese Patent Application No. 2019-524128, dated May 24, 2021. 14 pages with English translation.

MIIP, First Examination Report for Mexican Patent Application No. MX/a/2019/000902, dated May 21, 2021. 9 pages with English translation.

Russian Intellectual Property Office, Official Action and Search Report for RU2019104862 with English translation, dated Nov. 26, 2020. 11 pages.

Indian Patent Office, First Examination Report for IN 201917006786, dated Oct. 26, 2020.

IP Office Mexico, Third Office Action for Mexican Patent Application No. MX/a/2019/000902, dated Mar. 15, 2022. 10 pages with English translation.

Ip Office Russia, Official Action for Russian Patent Application No. RU2019104862, dated Feb. 21, 2022. 13 pages with English translation.

IP Office Mexico, Second Office Action for Mexican Patent Application No. MX/a/2019/000902, dated Oct. 6, 2021. 8 pages with English translation.

CDC, Fungal Nail Infections, https://www.cdc.gov/fungal/nail-infections.html, May 27, 2020.

Glick PL et al., "Iodine toxicity secondary to continuous povidone-iodine mediastinal irrigation in dogs." J Surg Res. Nov. 1990;49(5):428-34.

Gottardi, W. "Iodine and disinfection: theoretical study on mode of action, efficiency, stability, and analytical aspects in the aqueous system." Arch Pharm (Weinheim), 1999. 332(5): pp. 151-157.

Fearmonti et al., "A Review of Scar Scales and Scar Measuring Devices," Eplasty, 2010:10 e43.

IP Office Korea, Notice of Preliminary Rejection for Application No. 10-2019-7005137, with English translation, dated Oct. 25, 2021.

Mayo Clinic, Fungal Nail Diagnosis and Treatment; https://www.mayoclinic.org/diseases-conditions/nail-fungus/diagnosis-treatment/drc-20353300, Jul. 14, 2020.

USPTO/ISR Invitation to Pay Additional Fees for PCT/US2021/046035, dated Oct. 13, 2021.

IP Office Brazil, Preliminary Office Action for Brazilian Patent Application No. BR112019001054-8, dated Nov. 23, 2021, 5 pages with English translation.

IP Office China, Second Office Action for Chinese Patent Application No. 201780054315.6, dated Dec. 22, 2021. 8 pages with English translation.

IP Office Japan, Notice of Reasons for Rejection for Application No. 2019-524128, with English translation, dated May 24, 2021. 14 pages with English translation.

IP Office Japan, Decision of Refusal for Application No. 2019-524128, with English translation, dated Jan. 20, 2022. 9 pages with English translation.

USPTO/ISR International Search Report and Written Opinion for PCT/US2021/046035, dated Jan. 6, 2022. 16 pages.

Furnée CA. Prevention and control of iodine deficiency: a review of a study on the effectiveness of oral iodized oil in Malawi. Eur J Clin Nutr. Nov. 1997;51 Suppl 4:S9-10. PMID: 9598786.

Gottardi, W., 1991. Iodine and iodine compounds. In: Block, S.S. (Ed.), Disinfection, Sterilization, and Preservation. Lippincott Williams & Wilkins, Philadelphia, pp. 152-166 (1991).

Mhatre, Amol M., Sankararao Chappa, Shashikala Ojha & Ashok K. Pandey (2018): Functionalized glass fiber membrane for extraction of iodine species, Separation Science and Technology.

Simescu M, Varciu M, Nicolaescu E, Gnat D, Podoba J, Mihaescu M, Delange F. Iodized oil as a complement to iodized salt in schoolchildren in endemic goiter in Romania. Horm Res. 2002;58(2):78-82.

Untoro J, Schultink W, West CE, Gross R, Hautvast JG. Efficacy of oral iodized peanut oil is greater than that of iodized poppy seed oil among Indonesian schoolchildren. Am J Clin Nutr. Nov. 2006;84(5):1208-14. doi: 10.1093/ajcn/84.5.1208. PMID: 17093176. 10.1159/000064657. PMID: 12207166.

Taiwan IP Office, Pre-Notification Office Action for TW106124496 with English translation, dated Jul. 29, 2021.

USPTO/ISA Invitation to Pay Additional Fees for PCT/US2022/070687, dated Mar. 31, 2022. 2 pages.

USPTO/ISA International Search Report and Written Opinion for PCT/US2022/070687, dated Jun. 21, 2022, 2022. 14 pages.

IP Office Taiwan, Decision on First Patent Exam/Official Action for Taiwan Patent Application No. 106124496, dated Apr. 1, 2022. 8 pages with translation.

Aoki S. et al., "Antibacterial Properties of Silicone Membranes after a Simple Two-Step Immersion Process in Iodine and Silver Nitrate Solutions," Biocontrol Science. Jan. 23, 2018;(3):97-105.

Duckworth, P. et al., "A novel flow-system to establish experimental biofilms for modeling chronic wound infection and testing the efficacy of wound dressings," Microbiological Research. Jul. 2018; 215:141-47.

Edis, Z. et al., "Antimicrobial Biomaterial on Sutures, Bandages and Face Masks with Potential for Infection Control," Polymers. 2022; 14:1-29.

Morain, W. et al., "Iodinated Silicone—An Antibacterial Alloplastic Materials," Plastic and reconstructive surgery. Feb. 1977; 59(2):216-22.

Nakamura, K et al., "Antimicrobial Characteristics of Iodine-Releasing Silicone Membrane," Bokin Bobai. Jan. 2011; 39(6):337-42, with English translation.

Tyagi, M. et al., "Iodinated Natural Rubber Latex: Preparation, Characterisation & Antibacterial Activity Assessment," Artificial Cells, Blood Substitutes, and Biotechnology. 2000; 28(6):521-33.

IP Office Australia, Exam Report No. 1 for Australian Application No. 2017300497, dated Jun. 2, 2022.

IP Office Korea, Notice of Last Preliminary for Korean Application No. 10-2019-7005137, with English translation, dated Oct. 17, 2022.

FIGURE 1C
T24 Hours
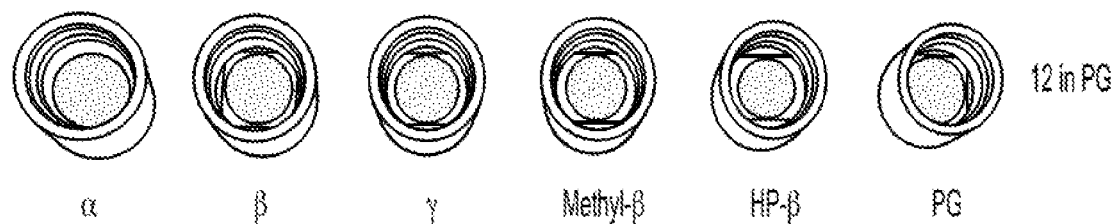
α   β   γ   Methyl-β   HP-β   PG          12 in PG
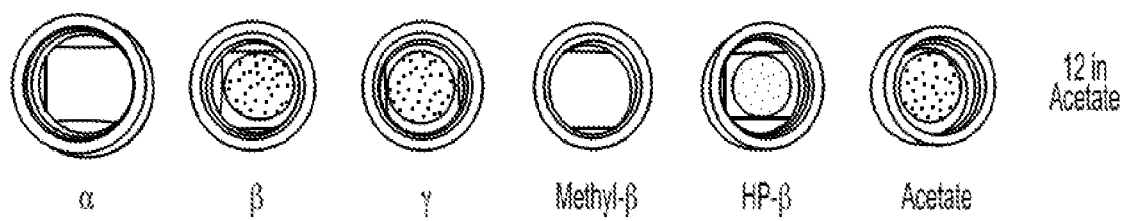
α   β   γ   Methyl-β   HP-β   Acetate     12 in Acetate
   12 in Glycerin
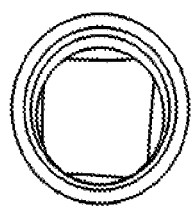
FIGURE 2A (T0)

FIGURE 2B (T5 MINUTES)
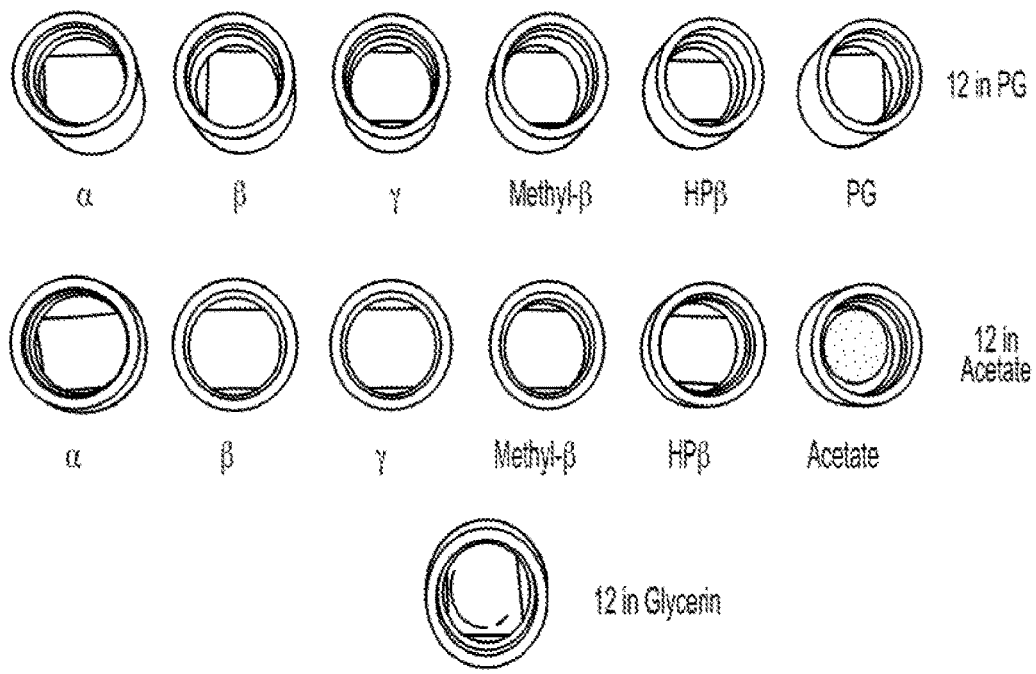
FIGURE 2C (T20 MINUTES)
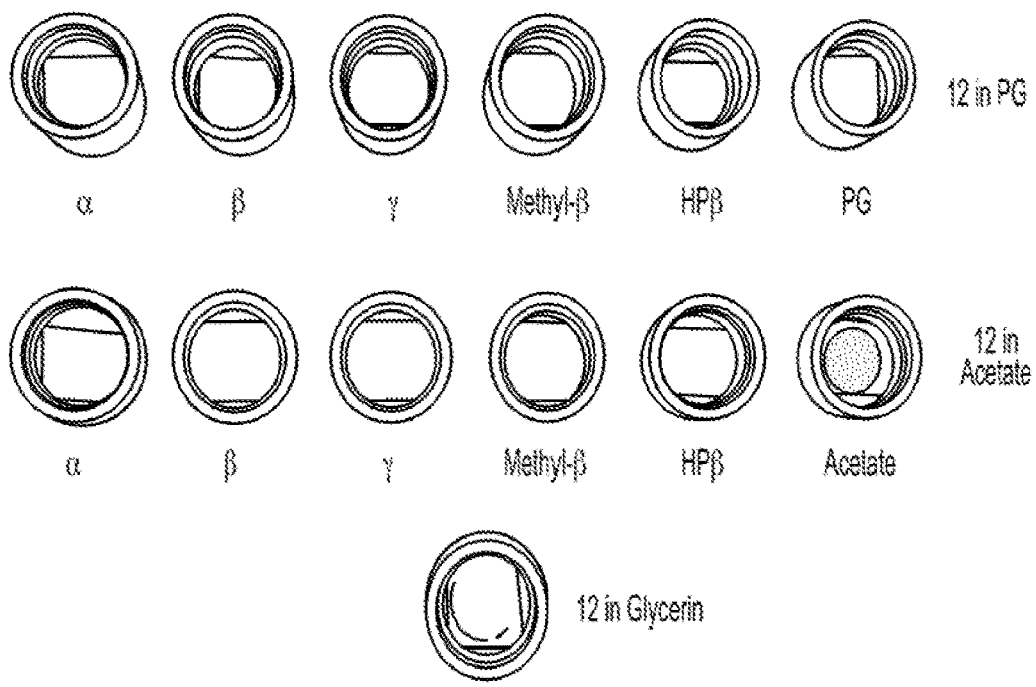

FIGURE 2D (T40 MINUTES)
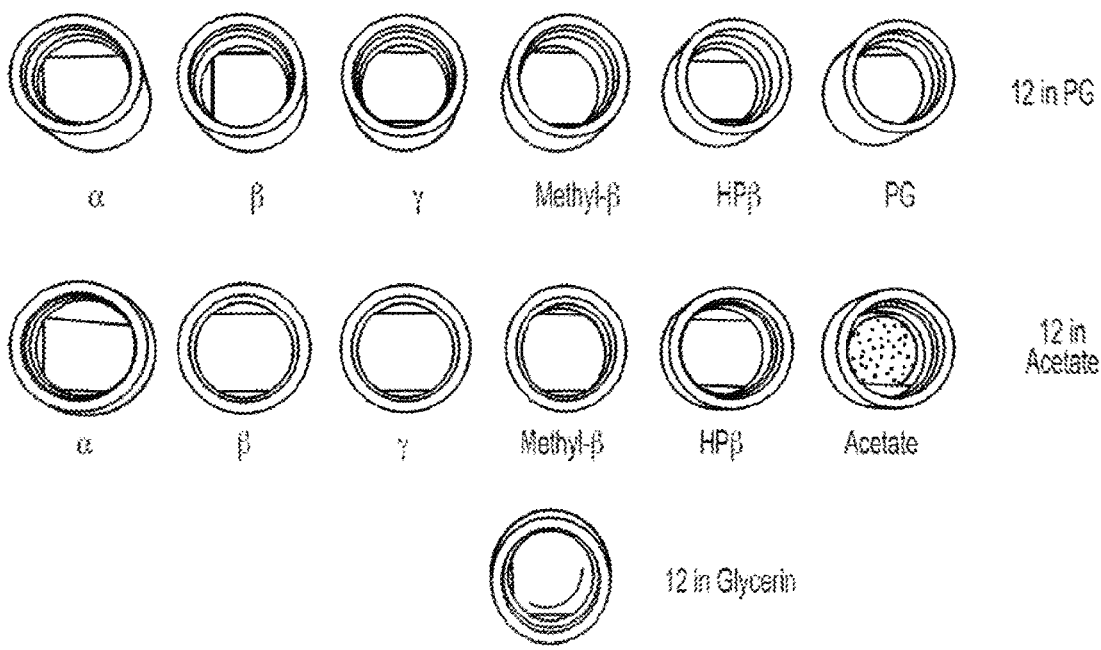
FIGURE 2E (T1 HOUR)
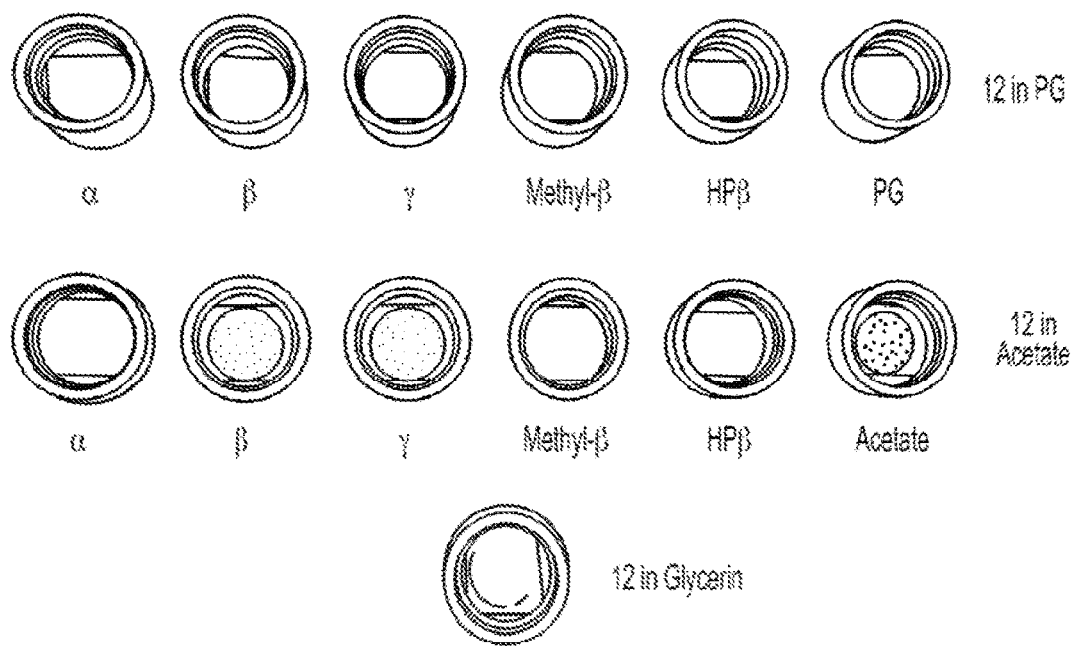

FIGURE 2F (T2 HOURS)
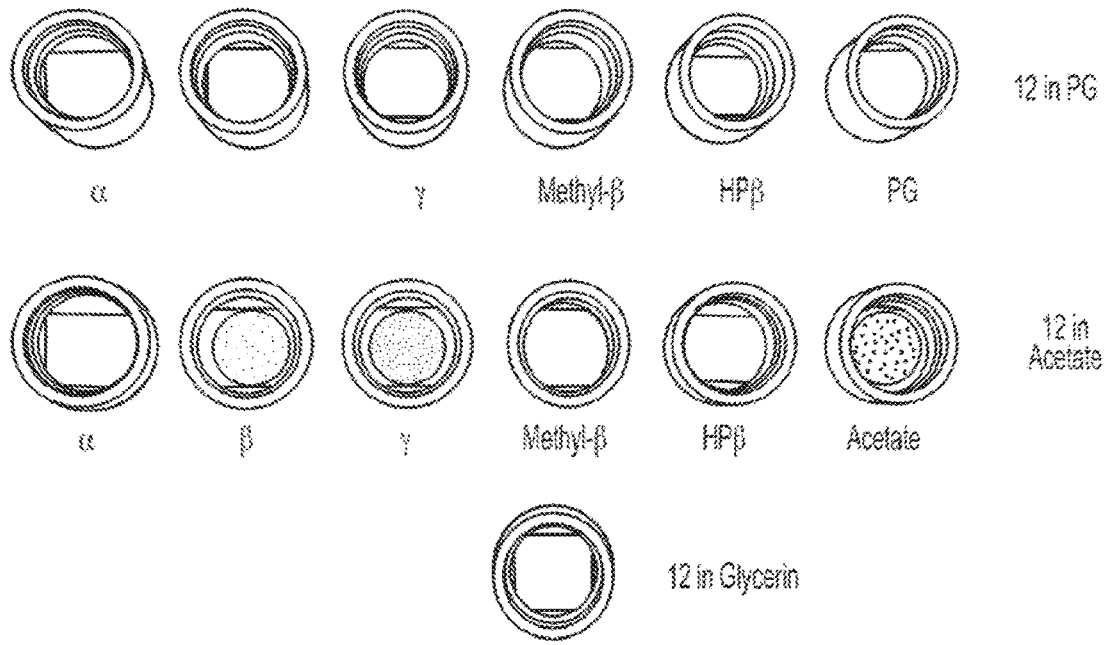
FIGURE 2G (T3 HOURS)
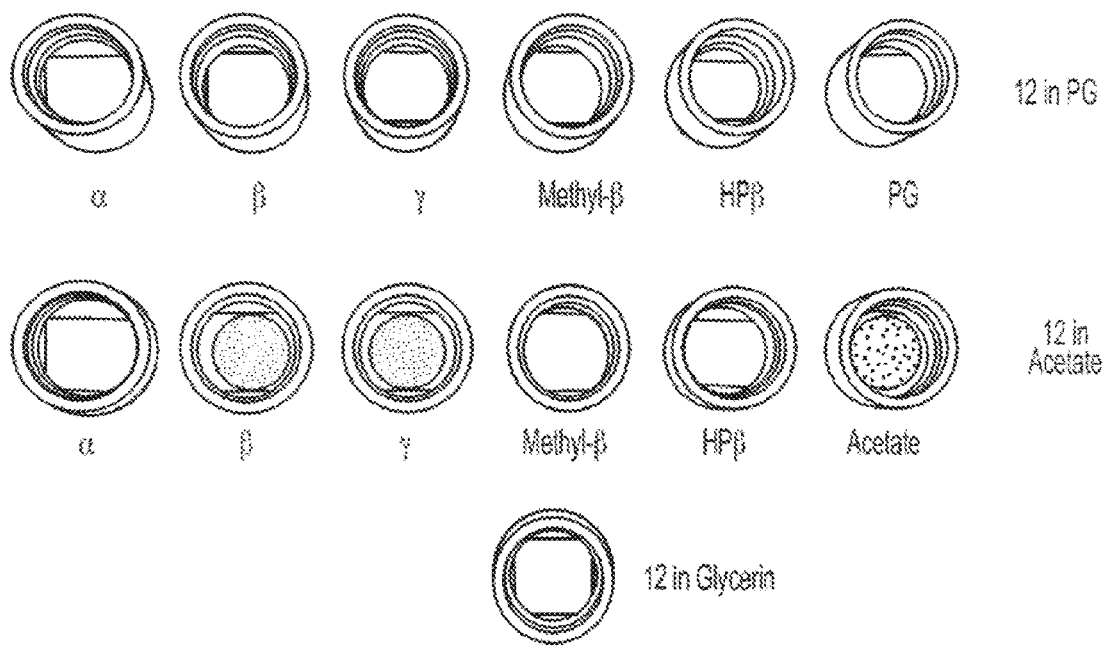

FIGURE 2H (T4 HOURS)
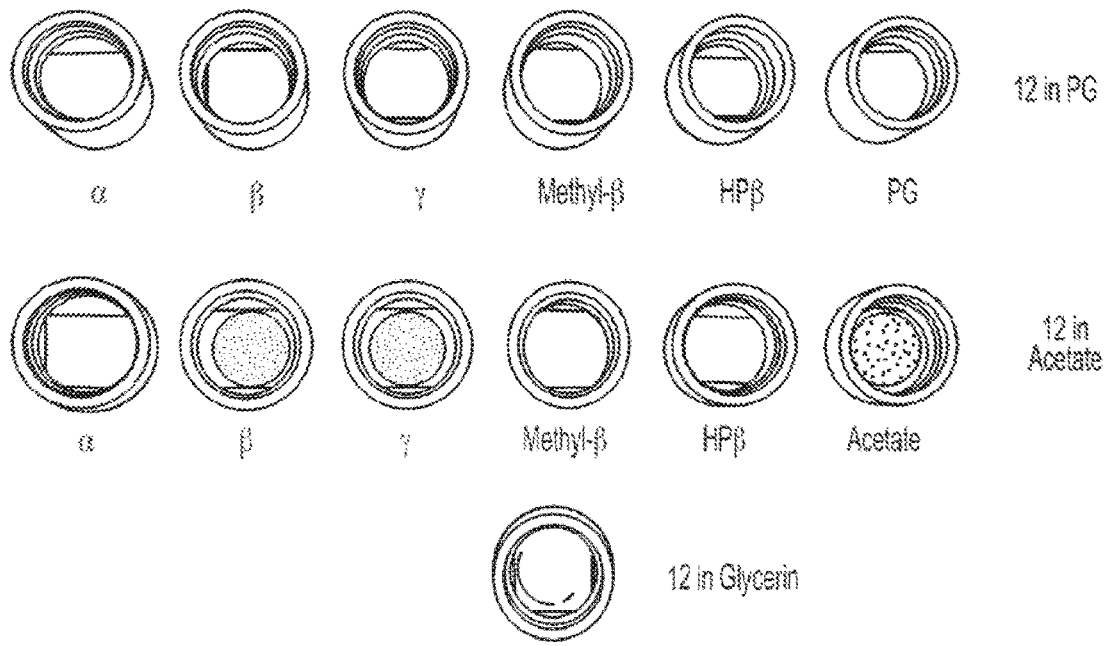
FIGURE 2I (T5 HOURS)
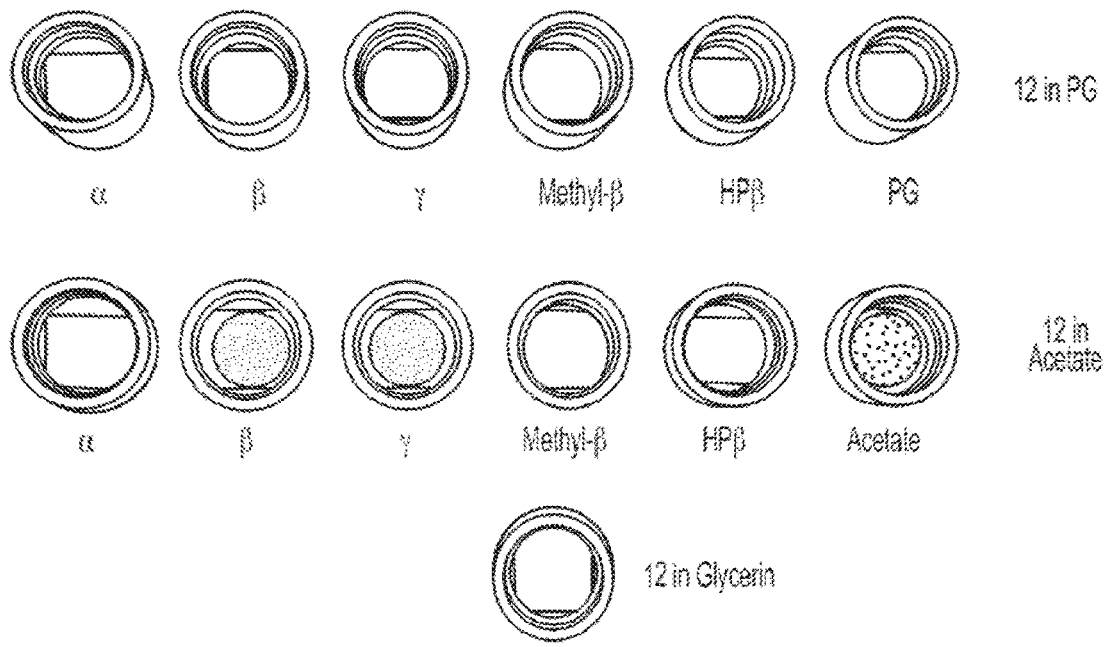

FIGURE 2J (T6 HOURS)
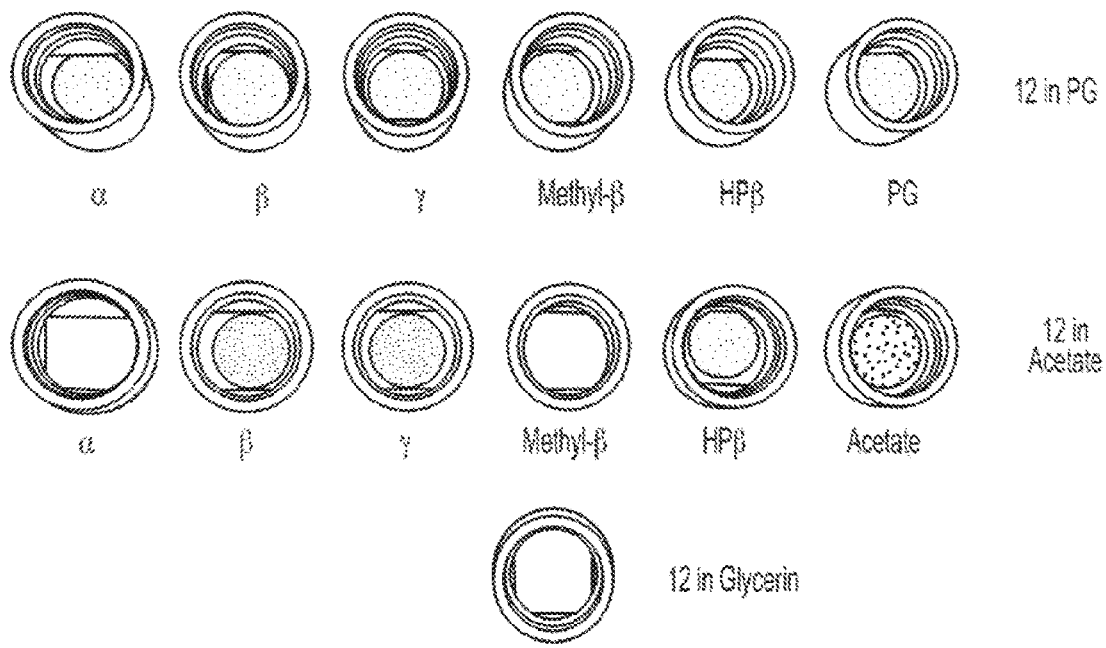
FIGURE 2K (T24 HOURS)
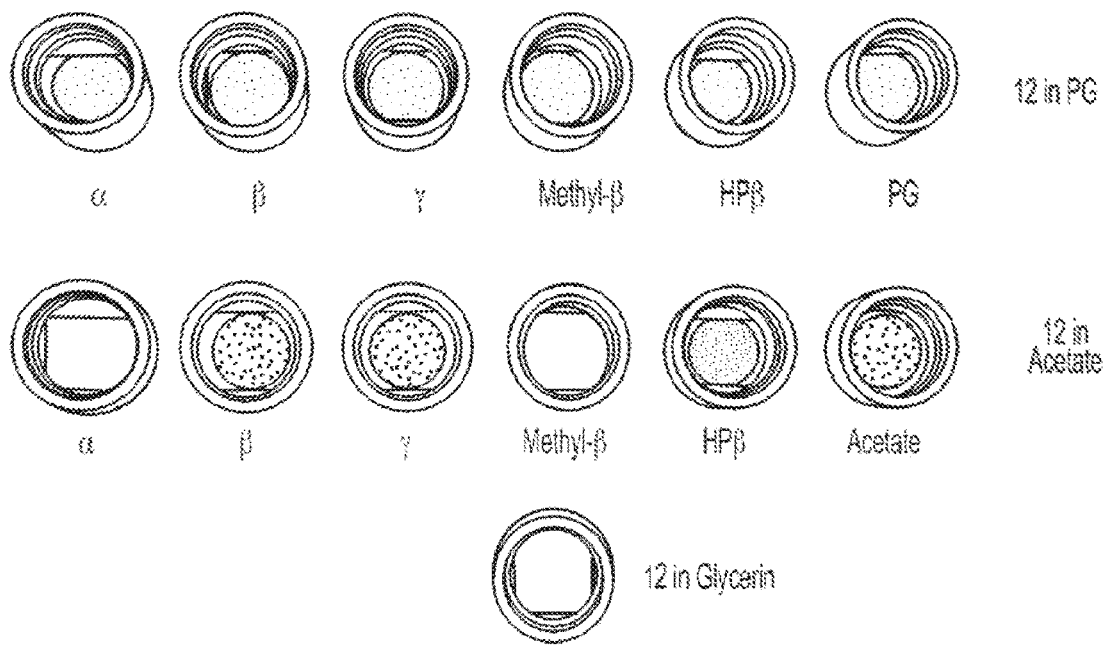

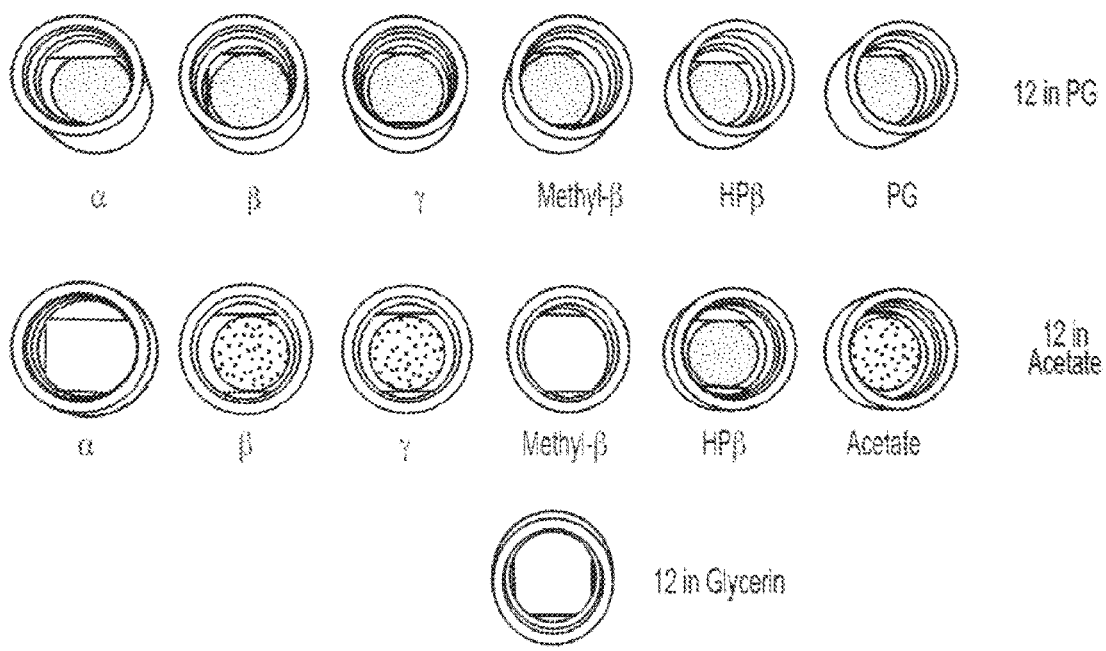

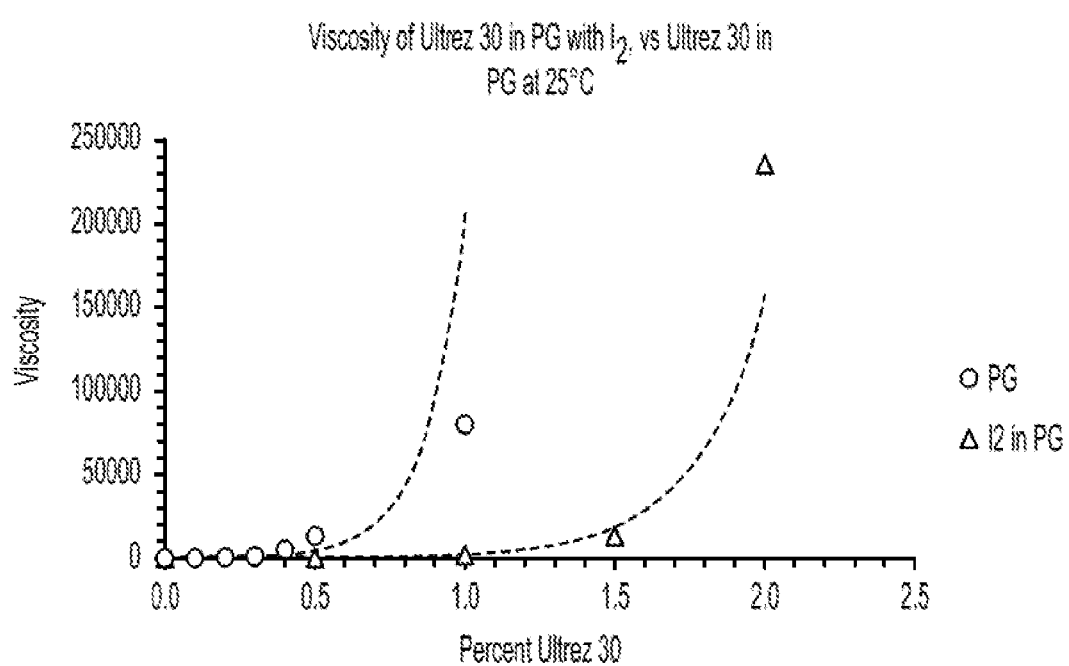

EMOLLIENT TOPICAL DISINFECTANTS

CROSS-REFERENCE TO RELATED APPLICATIONS

This application is a 371 application of PCT Application Serial No. PCT/US17/042726 filed Jul. 19, 2017, which claims priority to U.S. Provisional Patent Application No. 62/365,035, filed Jul. 21, 2016, each of which are incorporated by reference in their entirety.

FIELD OF THE INVENTION

This invention relates generally to an emollient topical composition of matter that contains molecular iodine with a reduced effective vapor pressure. In specific embodiments, the composition reduces the loss of molecular iodine to the atmosphere under storage conditions after application to mammalian tissue.

BACKGROUND OF THE INVENTION

Antibiotic resistance is a worldwide problem. New forms of antibiotic resistance can cross international boundaries and spread between continents with ease, many with remarkable speed. The CDC states that each year in the United States, at least 2 million people acquire serious infections with bacteria that are resistant to one or more of the antibiotics designed to treat those infections. At least 23,000 people die each year in the US as a direct result of these antibiotic-resistant infections. Many more die from other conditions that were complicated by an antibiotic-resistant infection.

Antibiotic-resistant infections add considerable and avoidable costs to the already overburdened U.S. healthcare system. In most cases, antibiotic-resistant infections require prolonged and/or costlier treatments, extend hospital stays, necessitate additional doctor visits and healthcare use, and result in greater disability and death, when compared with infections that are easily treatable with antibiotics. Estimates of the total economic costs of antibiotic resistance to the U.S. economy vary but have ranged as high as $20 billion in direct healthcare costs, with additional costs to society for lost productivity as high as $35 billion a year.

The use of antibiotics is the single most important factor leading to antibiotic resistance around the world. Antibiotics are among the most commonly prescribed drugs used in human medicine. However, up to 50% of all the antibiotics prescribed for people are not needed or are not optimally effective as prescribed. Antibiotics are also commonly used in food for animals to prevent, control, and treat disease, and to promote the growth of food-producing animals compounding the problem.

Staphylococcus Aureus (S. Aureus) is the leading cause of surgical site infections with approximately 80% of S. Aureus infections caused by the patient's own nasal flora. Methicillin-resistant Staphylococcus aureus (MRSA) is the most common causative pathogen of hospital-treated acute bacterial skin and skin-structured infections (ABSSSI). Currently, MRSA kills more people each year than AIDS and HIV combined.

It has been demonstrated that molecular iodine is highly effective against MRSA and offers the advantage of a broad spectrum antimicrobial nasal agent with substantial in vitro and in vivo evidence. Molecular iodine's activity is effective against both common bacterial and antibiotic-resistant species. Molecular iodine does not generate resistant bacterial strains.

The elimination of topical pathogens including bacteria, viruses and fungi, from mammals is an established prophylactic and therapeutic procedure in hygiene and medicine. Numerous topical compositions, intravenous (IV) treatments, devices and clinical procedures are used daily to eliminate topical pathogens in an attempt to improve patient outcomes. Nevertheless, nasal-borne Staphylococcus aureus (MRSA) that have not been effectively addressed.

Approximately one in three (33%) people carry Staphylococcus aureus in their nose (http:/www.cdc.gov/mrsa/tracking) and two in 100 people carry MRSA. In a study of patients previously identified as MRSA carriers at one time or another 91% were positive for MRSA in nasal samples and almost 25% of these patients had MRSA in the nose but not at any other body site (Antimicrob. Agents Chemother. November 2007 vol. 51 no. 113880-3886). The only approved treatment for the elimination of MRSA from the nasal colony is Bactroban™ whose active agent is the antibiotic mupirocin. The percent of Staphylococcus aureus seen in patients that are resistance to mupirocin was estimated to be about 18% in 2002 (Antimicrob. Agents Chemother. November 2007 vol. 51 no. 113880-3886). Increased use of antibiotics to eliminate nasal-borne MRSA is therefore a sub-optimal long-term strategy.

Iodine-based formulations are used for disinfection of epidermal tissue in many clinical situations such, e.g. pre-surgical, catheterization, burns, needle puncture, wound care or topical infection. These iodine-based formulations depend entirely upon molecular iodine for their biocidal activity (Hickey et. al. J Pharm Pharmacol. 1997 December; 49(12):1195-9). In fact, bacteria can survive for extended periods of time in 10% polyvinylpyrollidone iodine ("PVP-I") formulations if the molecular iodine is highly complexed such that the effective concentration of molecular iodine is less than 1 ppm (Favero M S. Infect Control. 1982 January-February; 3(1):30-2). Simply adding molecular iodine to an aqueous formulation is insufficient to insure its presence in a formulation as other iodine species are formed once molecular iodine undergoes hydrolysis e.g., iodide, hypoiodous acid, iodide, triiodide, iodate.

Almost all topical iodine compositions taught in the literature are based upon iodophors (any of a group of disinfectants containing tri-iodide in combination with a surfactant and inequilibrium with iodide and traces of molecular iodine) or formulations wherein molecular iodine is complexed with iodide. These additional iodine species (iodide, tri-iodide and PVP-I) increase the potential risk of systemic toxicity and contribute to staining but do not contribute antimicrobial activity (they are included to stabilize molecular iodine). The belief that iodophors reduce the staining and negative organoleptic properties of molecular iodine are unsupported by data and inconsistent with published data although this may be the case for Lugols Solution. See, e.g. Duan Y, et. al. J Hosp Infect. 1999 November; 43(3):219-29; U.S. Pat. Nos. 6,432,426; and 6,261,577.

Many topical iodine-base formulations have been posited in the art since development of PVP-I. For example, U.S. Pat. Nos. 9,114,156 and 6,228,354 describe film film-forming polymers that contains PVP-I. U.S. Pat. No. 7,147,873 teaches a film film-forming polymer that contains both molecular iodine and an iodophor. U.S. Pat. No. 8,808,722 describes formulations of complexed iodine that are formed from combinations of molecular iodine/iodophors that contain 0.1% to 2% by concentration of titratable iodine in combination with an iodide salt present at a minimum concentration of 2.0% by weight.

U.S. Pat. No. 8,840,932 teaches film forming antimicrobial compositions that contain both molecular iodine and PVP-I but molecular iodine is not included as an ingredient in any of the examples in the application nor are conditions described that would serve to provide a stable environment for molecular iodine in the absence of PVP-I.

U.S. Pat. No. 5,922,314 teaches an antimicrobial film-forming composition, comprising ethyl alcohol, carboxylated polyacrylates, a cross linking agent, an adhesion promoting agent, an active antimicrobial agent which can be either iodine or PVP-I, a pluronic polyol and molecular iodine and/or PVP-I. The '341 patent teaches increased stability of "iodine" but does not teach conditions that will stabilize molecular iodine in an aqueous environment. In fact, Example 1 demonstrates the lack of molecular iodine stability in the absence of 10% PVP-I. Specifically, when included in the disclosed formulations as composition A of this example, which contained only molecular iodine, the formulation demonstrated an almost 50% loss of iodine as compared to compositions that contained 10% PVP-I; the 50% loss of available iodine was comparable to the control.

Valid formulation approaches for topical antimicrobial compositions that provide pure molecular iodine in enzyme-based formulations are taught in U.S. Pat. Nos. 5,370,815 and 5,227,161. U.S. Publication No. 20060280809 (abandoned); U.S. Pat. No. 5,897,872 and PCT Publication No. WO 2012177251 teach the use of PVP-I in the sinus cavity to treat sinusitis. U.S. Pat. Nos. 8,303,994 and 8,691,290 teach methods for killing pathogens residing in the nasal cavity based on molecular iodine generated from the reaction of iodide with iodate such that final concentrations ranged from 25 ppm to about 250 ppm.

The present invention relates to compositions that contain molecular iodine intended for tissue antisepsis. The compositions taught herein are useful in preparing epidermal and mucosal tissue (including oral tissue, nasal passages including the anterior nares, esophagus, and vagina) prior to invasive procedures and for eliminating pathogens that have caused or are at risk of causing morbidity and/or mortality.

BRIEF DESCRIPTION OF THE DRAWINGS

FIGS. 1A-1C illustrate the results from Example 4, according to one embodiment of the invention.

FIGS. 2A-2L illustrate the results from Example 5, according to one embodiment of the invention.

FIGS. 4A-C illustrate the results from Example 7, according to one embodiment of the invention.

BRIEF SUMMARY OF THE INVENTION

Figure 1A:
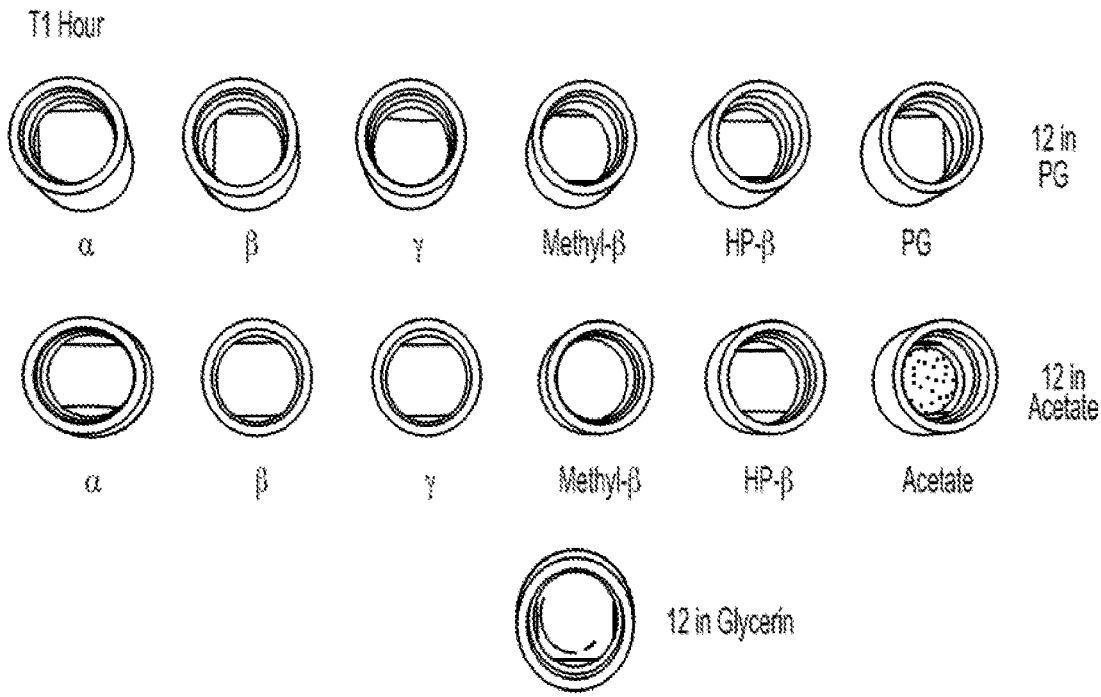

More specifically this invention contemplates a pharmaceutically acceptable formulation based upon an emollient organic carrier molecule that: (1) has a vapor pressure at standard atmospheric pressure that is at least 30% lower than the vapor pressure of molecular iodine; (2) has a boiling point that is greater than 100° C. at standard atmospheric pressure; and (3) provides an environment that stabilizes molecular iodine for at least nine (9) months at room temperature.

Iodine-based topical antimicrobials are widely used in clinical settings. Molecular iodine, the sole biocidal agent in iodophor formulations, has a low vapor pressure and is rapidly lost to the atmosphere when dissolved in an aqueous formulation exposed to the atmosphere. Iodophors stabilize a low level of unbound (free) molecular iodine that can inactivate pathogens by maintaining a reservoir of bound molecular iodine in the form of tri-iodide that is in equilibrium with molecular iodine wherein the relative concentration of these two species (tri-iodide/molecular iodine) is on the order of 10,000 to 1.

Once an iodophor is spread onto a mammalian tissue, the resulting surface to volume ratio of the applied iodophor is extremely high. This high surface to volume ratio guarantees the extremely rapid loss of any free molecular iodine to the atmosphere. Film forming iodophors that claim to provide a persistent antimicrobial barrier have been developed. However, once a film is formed from an iodophor there is no free molecular iodine present. In these instances, the free molecular iodine has either: (a) been lost to the atmosphere; or (b) turned into a solid due to the limited solubility of molecular iodine and then sublimed into the atmosphere. Before a film formed with an iodophor can provide antimicrobial activity it must be re-dissolved, presumably by a wound exudate. As a result, the composition would necessarily have a very high concentration of iodophors that would inhibit the release of free molecular iodine.

In various embodiments, provided herein is a topical iodine-based composition that: (a) delivers free molecule iodine at concentrations that are 10 to 400 times higher than those found in typical iodophors; (b) is emollient; and (c) lowers the effective vapor pressure of molecular iodine such that molecular iodine will remain in the composition at least an order of magnitude longer than a comparable aqueous composition when it is exposed to the atmosphere.

In various embodiments, the compositions contemplated in this application effectively provide topical compositions that can maintain high concentrations of free molecular iodine in contact with mammalian tissue for extended periods of time as compared to iodophors.

DETAILED DESCRIPTION OF THE INVENTION

The present invention will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, chemistry, etc., portions pertaining to such compounds, chemistry, etc. are those portions of the document which are incorporated herein by reference.

To more readily facilitate an understanding of the invention and its preferred embodiments, the meanings of terms used herein will become apparent from the context of this specification in view of common usage of various terms and the explicit definitions of other terms provided in the glossary below or in the ensuing description.

Glossary

It should be noted that, as used in this specification, the singular forms "a," "an," and "the" include plural referents unless the context clearly dictates otherwise. Thus, for example, reference to a "gelling agent" refers to a single gelling agent as well as to several different gelling agents, reference to an "excipient" includes a single excipient as well as two or more different excipients, and the like.

"Optional" or "optionally" means that the subsequently described circumstance may or may not occur, so that the description includes instances where the circumstance occurs and instances where it does not.

The term "pharmaceutically acceptable" in reference to an entity or ingredient is one that causes no significant adverse toxicological effects in the patient at specified levels, or if levels are not specified, in levels known to be acceptable by those skilled in the art. All ingredients described in this application are pharmaceutically acceptable.

The term "molecular iodine" refers to diatomic iodine, which is represented by the chemical symbol $I_2$ (CAS Registry Number: 7553-56-2) whether dissolved, suspended or in a solid state. Molecular iodine is also referred to as "elemental iodine" when in the solid state.

The term "iodide" or "iodide anion" refers to the species which is represented by the chemical symbol $I^-$ (CAS Registry Number: 20461-54-5). Suitable counter-ions for the iodide anion include sodium, potassium, calcium, and the like.

The term "iodate" refers to the iodate anion which carries a negative charge and is represented by the chemical symbol $IO_3$. The commonly available salts of iodate serve as suitable sources for iodate for this invention and, by way of example, include sodium iodate (EC Number: 231-672-5), potassium iodate (EC Number: 231-831-9), and calcium iodate (EC Number: 232-191-3), whether dissolved or in a solid state.

The term "complexed iodine" or "bound iodine" as used herein refers to a mixture of molecular iodine with other chemical species that bind molecular iodine and render the molecular iodine incapable of killing pathogens. Complexing molecule iodine to other chemical species such as iodide and/or polyvinylpyrollidone is a formulation strategy used to increase the stability of molecular iodine. Lugol's solution was the first widely used example of complexed iodine.

The term "iodophor" as used herein refers to a mixture of molecular iodine with a polymer(s) that serves to reduce the level of free molecular iodine in solution. Polymers that are used to form iodophors include polyvinylpyrrolidone, copolymers of N-vinyl lactams, acrylates and acrylamides, various polyether glycols including nonylphenolethoxylates and the like and combinations thereof. Povidone-iodine (PVP-I) is an iodophor that is most commonly used form of complexed iodine today.

The term "polymer" as used herein includes homopolymers and copolymers and "copolymer" includes a polymer of any length (including oligomers) of two or more types of polymerizable monomers, and therefore includes terpolymers, tetrapolymers, etc., which can include random copolymers, block copolymers, or sequential copolymers.

The term "all iodine species" in a sample refers to the total iodine, irrespective of form, from all iodine containing components within a sample.

The term "ratio of molecular iodine to all iodine species" in a sample refers to the ratio of molecular iodine (I2) in the sample divided by the concentration of iodine from all iodine species within the sample.

The term "organic carrier for molecular iodine" refers to a pharmaceutically acceptable organic molecule in which molecular iodine is soluble and which does not interact with molecular iodine to change its structure, i.e. supports stability of molecular iodine. Propylene glycol and glycerin are the two most preferred organic carriers.

The term "organic additives" as used herein refers to organic molecules that can be included with an organic carrier for molecular iodine to add additional features. Such organic molecules include; propylene glycol monomethyl ether acetate, amyl alcohol, ethyl acetate, butyl acetate, ethanol, dimethylsulfoxide, 1-propanol and 2-propanol.

The term "gelling agent" or "viscosity enhancer" refers to a pharmaceutically acceptable organic molecule that serves to increase the viscosity of a composition.

The term "body temperature" refers to the temperature of a mammalian tissue surface that is under treatment. For instance, the temperature of normal healthy skin is between 32° C. and 34° C. and the temperature of the mucosal lining of the nose is between 32.5° C. and 35° C. depending upon the location of measurement and patient.

The term "reconstituted shelf-life" refers to the amount of time that molecular iodine is within a desired range after it is activated/mixed in a dual- or multi-phase formulation.

The term "shelf-life" refers to the amount of time that the product can be stored in a suitable package under normal storage conditions and still provide at least 90% of claimed active.

The term "effective amount" is used herein to mean the concentration of an ingredient in a pharmaceutical preparation that is needed to inactivate pathogens of clinical interest. The precise amount will depend upon numerous factors, e.g., the components and physical characteristics of the pharmaceutical preparation, intended indication, intended patient population, and the like, and can be determined by one skilled in the art, based upon the information or the methods provided herein.

The term "contact time for required for efficacy" is used herein to mean the minimum amount of time required for a composition to achieve clinical effectiveness once it is in contact with mammalian tissue.

The term "patient" refers to a living organism that can be treated by administration of a suitable embodiment of the teachings contained in this invention.

"Normal storage conditions" in reference to the compositions herein is an environment with a temperature of 5-40° C., 10-90% humidity, 1 Atmosphere of Pressure (ATM), and approximately 20% oxygen and 80% nitrogen.

The term "pH control agent" shall refer to chemical(s) that control the effective pH of a composition or a component of a composition. Suitable pH control agents include salts of carbonate, phosphate and acetate, formate, succinate, e.g., calcium carbonate, potassium acetate, sodium succinate, and the like.

The term "dual-chamber package" refers to a package that keeps formulation components separate while in storage. The dual-chamber package combines all ingredients in a formulation prior to use. The term dual-chamber package also refers to packages that contain more than two chambers.

The terms "single phase" and "dual-phase" refer to packaging configurations anticipated in this application for use with formulations that consist of either a single component or two components that are mixed prior to use. The term dual-phase also refers to formulations that consist of more than two phases.

For the sake of brevity, all patents and other references cited herein are incorporated by reference in their entirety.

The biocidal species in iodine-based disinfectants is molecular iodine. Since molecular iodine is unstable in an aqueous environment formulators have used iodophors to provide a small concentration of molecular iodine in equilibrium with a very large concentration of iodide/tri-iodide and organic molecules that bind molecular iodine or tri-iodide. This results in a formulation wherein the active agent, molecular iodine, is present at a concentration that is typically less than 0.1% of the total iodine species. Iodophors that contain concentrations of molecular iodine below a critical level can be contaminated with bacteria and have caused transmission of infections.

The active agent identified in the present application is molecular iodine. The ratio of molecular iodine to all iodine species in the compositions described in this application is at least 80% of all iodine species and preferably at least 90% and optimally 100%. The source of molecular iodine in the products contemplated in the current application is dissolution of molecular iodine in an emollient organic carrier. One problem associated with formulating pure molecular iodine in a liquid is the propensity to lose molecular iodine to the atmosphere.

The only form of iodine that forms a gas at room temperature is molecular iodine. Molecular iodine has a vapor pressure of 0.3 mm at 25° C. and 1 mm at 38.7° C. At standard atmospheric pressure, a maximum of 394 ppm of iodine can build up in a closed container at 25° C. Iodine vapor is intensely irritating to mucous membranes and adversely affects the upper and lower respiratory system. Inhalation of iodine vapor can cause tearing, tightness in the chest, sore throat, increased pulmonary flow resistance, decreased ventilation rate and headache. Humans can work undisturbed at 0.1 ppm; with difficulty at 0.15-0.2 ppm and cannot tolerate concentration of 0.3 ppm and higher. Severe eye irritation is observed at a concentration of 1.63 ppm after 2 minutes and the lowest lethal atmospheric concentration for rats is 80 ppm for 1 hour. The permissible exposure limit is 0.1 ppm (NIOSH, OSHA) but odor is not detected until a level of about 0.9 ppm is reached, so irritation can occur before the odor is detected.

Two formulation tactics are described in this application allow high concentrations of molecular iodine to be incorporated into the compositions of matter contemplated in this application. The first tactic is the use of a low vapor pressure, non-aqueous organic carrier with a boiling point greater than 100° C. to contain the molecular iodine. The hydrophobic environment of the organic carriers identified in this application has a higher affinity for molecular iodine as compared to water; this reduces the effective vapor pressure of molecular iodine and reduces the loss of molecular iodine to the atmosphere.

The second tactic to lower the vapor pressure of molecular iodine is the use cyclodextrins that do not neutralize molecular iodine but do provide an inclusion cavity from which molecular iodine cannot easily escape. The use of a preferred cyclodextrin lowers the vapor pressure of molecular iodine as demonstrated in the examples contained in this application.

The preferred emollient organic carriers of this application (a) have a vapor phase that is less than 30% of the vapor phase of molecular iodine and (b) boil at a temperature that is higher than 100° C. The preferred emollient organic carriers of this application can solubilize at least two-times as much molecular iodine per unit volume as water. The combination of these characteristics serves to substantially lower the rate of loss of molecular iodine to the atmosphere once applied to an epidermal surface as compared to what the loss would be in an aqueous composition. The preferred emollient organic carriers of this application can be combined with water prior to application if it is desirable to increase the rate of release of molecular iodine from said composition for a particular use.

The preferred formulations identified in this application use either propylene glycol or glycerin as the emollient organic carrier for molecular iodine. Additional organic carriers can be included in the compositions anticipated in this application to provide ancillary product features. Additional organic carriers that can be included in the compositions anticipated by this application include propylene glycol monomethyl ether acetate, amyl alcohol, ethyl acetate, butyl acetate, dimethylsulfoxide, 1-propanol and 2-propanol, dimethyl sulfoxide, ethanol, iso-propanol, ethanol and the like.

Several different packaging configurations are contemplated in the present invention. In one configuration the product will be contained within a single compartment. In another configuration the product will be contained in two separate compartments that are mixed prior to application on the mammalian tissue of interest. In yet another configuration the product will be contained in three different compartments or materials that are mixed or contacted with each other prior to application on the tissue of interest. These different packaging configurations increase the number of different excipients that can be included in a formulation as many excipients reduce the stability of the molecular iodine to such a degree that it is not possible to achieve adequate stability to place the product into commercial distribution as the active agent will be lost.

Multi-compartment packages allow for the possibility of mixing an aqueous phase with the organic carrier phase immediately prior to application of the topical compositions described in this application. Water-soluble polymers, gelling agents, fragrances and pH control agents can be incorporated into such an aqueous phase to impart desirable formulation features.

Additional elements of the current invention include viscosity enhancing agents familiar to one skilled in the art such as hydroxypropyl cellulouse, hydroxymethyl cellulouse, hydroxyethyl cellulose, hydroxypropylmethyl cellulose, poloxamer (copolymers of polyoxypropylene and polyoxyethylene), cross-linked homopolymers of acrylic acid like Ultrez 30, carboxymethyl cellulose or guar gum. Preferred viscosities for certain embodiments of the compositions described herein are no greater than 100,000 Centipoise (cps), more preferably no greater than 50,000 cps, even more preferably no greater than 10,00 cps and most preferably no greater than 500 cps.

An additional element of the current invention includes unsaturated fatty acids that impart a long-lasting residual bactericidal activity. A representative list of such agents includes lactic acid, myristic acid, 1-monolaurin, dodeconic acid and caprylic acid. Latic acid and caprylic acid can be incorporated directly in propylene glycol; the other unsaturated fatty acids must be incorporated into an aqueous phase that is combined with propylene glycol or glycerin prior to use.

Preferred compositions of the present invention are substantive while in a moist environments, such as the nose, anterior nares, and vaginal vault and remain on any of these tissues for longer periods of time than typical antiseptics such as 10% povidone-iodine solution (Purdue Frederick, Norwalk, Conn.). A "substantive" composition is one that when placed on a mammalian tissue such as the anterior nares has some residual molecular iodine still present after killing the majority of microbes present (which occurs in a few minutes) after instillation of 0.25 milliliter (mL) with a cotton bud and gently massaging the nostrils for 30 seconds to ensure an even distribution (as long as the patient does not discharge or deliberately or inadvertently wipe the product away). In specific embodiments described herein, preferred substantive compositions remain present in the anterior nares for 50 minutes, and more preferably for at least 60 minutes post instillation.

The literature is replete with iodophor compositions that form films to enhance their biocidal activity. The formulation approach inherent to film-based iodophors is to provide a complex iodophor composition that delivers a very small concentration of molecular iodine which dries onto the surface of the skin and which will presumably have the ability to release some molecular iodine if said film interacts with a moist environment. It has been demonstrated that molecular iodine is absorbed into skin and outgasses from skin for at least 24 hours. In addition, the concentration of molecular iodine absorbed and outgassed is directly proportional to the concentration of molecular applied to skin. Certain topical applications contemplated in this application anticipate converting skin into an active antiseptic barrier by impregnating molecular iodine into skin as opposed to the approach taken by film forming topical iodophor preparations.

Additives have been identified that allow molecular iodine to be present in the formulation once applied for a time required for efficacy and then which induce the molecular iodine to dissipate by forming iodide.

A particularly important property of the antiseptic compositions of the present invention for use on skin, wound, or mucosal tissue is the ability to reduce the bacterial load on tissue, particularly skin (e.g., to kill the natural skin flora), rapidly. In specific embodiments of the invention described herein, the compositions are capable of reducing normal skin flora by at least 1 log (10-fold), more preferably by at least 1.5 log, and most preferably by at least 2 log.

The present invention overcomes the limitations of the prior art by providing an emollient composition that contains high concentrations of substantially pure molecular iodine that can remain in contact with tissue for extended time periods.

The following examples are illustrative of the teachings of this application and are not meant to limit the invention in any manner.

EXAMPLES

Example 1

Iodine crystals (Alfa Aesar; Ward Hill, Mass.; Cat. Num. 14248; Lot 104Z003) were added to about 50 mL of propylene glycol in a screw-top vial to achieve at a w/v (iodine/organic carrier) ratio of 1 mg/mL.

A second screw-top vial was used to form a comparable solution of molecular iodine in glycerin. Stir bars were placed in the bottles and Teflon lined screw-top lids were used to seal the bottles. The two bottles were stirred at room temperature for 14 days. Aliquots from the two saturated solutions were diluted in their respective organic carriers to a concentration that yielded an optical density of about 1.0 at 290 nm.

A 3.0 mL aliquot of each diluted molecular iodine solution was periodically withdrawn and placed in a disposable plastic cuvettes (Brand 7591 70). The cuvettes were tightly capped with LDPE caps and then wrapped with Teflon (PTFE) tape to prevent loss of molecular iodine to the atmosphere. A UV-VIS scan was collected on each sample and the absorbance at 290 nm and 360 nm was used to monitor the stability of molecular iodine as a function of time. Samples were stored at ambient conditions.

Twenty time points were taken over a 4 month time frame and the absorbance values were averaged. Values greater than or less than 2 standard deviations from the mean were discarded and the mean was recalculated. A sample was considered to be unstable if there was a loss of 10% from the initial value measured.

The data demonstrated that molecular iodine was stable in both organic carriers. As an example, after 120 days there was a loss of less than 6% of the molecular iodine in propylene glycol and less than 5% in glycerin. The standard deviation of all data points obtained in propylene glycol was equivalent to less than 2% of the initial optical density and the equivalent measurement in glycerin was less than 1.7%.

Example 2

Iodine stability in different organic solvents was tested using the procedures described herein. Specifically, iodine crystals (Alfa Aesar 14248 Lot 104Z003) were added to 1 mg/mL concentration to the following solvents; USP glycerin (Signma-Aldrich, St. Louis, Mo.; Cat. #G2289), propylene glycol (Sigma-Aldrich, St. Louis, Mo.; Cat. #D1435) and ethanol (Sigma-Aldrich, St. Louis, Mo.; Cat. #792799-24X1PT).

Stir bars were placed in the bottles and the bottles were capped. Samples were stirred at room temperature for 7-14 days. The resulting saturated solutions were left unfiltered.

Aliquots from the saturated solutions were diluted with their respective solvents to a concentration which gave an OD peak height of around 1.0 at 290 nm and 360 nm wavelengths in a spectrophotometer.

3 ml aliquots of DMSO and ethanol with iodine added as determined in the above step were placed in clear ISO certified disposable plastic cuvettes (Brand 7591 70). The cuvettes were tightly capped with LDPE caps wrapped with Teflon (PTFE) tape.

Samples were stored at ambient conditions inside a drawer. Measurements were taken at various time points in a spectrophotometer. By day 60, the ethanol sample had lost more than 20% of the original molecular iodine as measured by the optical density at 290 nm and 360 nm. In contrast, glycerin, propylene glycol and dimethyl sulfoxide did not lose any molecular iodine at time points greater than 270 days.

Example 3

Iodine was dissolved in acetate buffer to create saturated solutions. Specifically, iodine crystals (Alfa Aesar 14248 Lot 104Z003) were added to pH 4.5 acetate buffer at a concentration of 1 mg/mL. Stir bars were placed in the bottles and the bottles were capped. Samples were stirred at room temperature for 7-14 days. The resulting saturated solutions were left unfiltered.

Different concentrations of carboxymethyl cellulose (Sigma Aldrich, St Louis, Mo.; Category #419273-1006; Lot #: MKBT6160V; CAS #9004-32-4), hydroxypropylmethyl cellulose (Moleularrecipes.com; F50; X00096CD4N; Marina del Rey, Calif.), Poloxamer-188 (Alfa Aesar, Ward Hill, Mass.; Category #: J66087; Lot #: W24A018; CAS #9003-11-6), and Carbopol Ultrez 30 (Lubrizol, Cleveland, Ohio; Category #CBP1118; Batch #0101499333) were added to aliquots of acetate buffer that contained molecular iodine prepared as described above. The final samples contained 5% CMC, 5% HPMC, 5% Poloxamer-188, and 0.5% Carbopol Ultrez 30. The resulting samples were placed in a spectrophotometer (Spectra Max Plus 384 UV-Vis Spectrophotomer; Molecular Devices; Sunnyvale, Calif.) to confirm that the optical density at 290 nm and A360 nm was about 1.0 A.

Aliquots (3 ml) of each polymer formulation that contained molecular iodine were placed in clear ISO certified disposable plastic cuvettes (Brand 7591 70). The cuvettes were tightly capped with LDPE caps wrapped with Teflon (PTFE) tape and the samples were stored at ambient conditions inside a drawer.

Optical density measurements were taken at 290 nm and 360 nm at various time points to measure the amount of molecular iodine that remained in each sample. More than 90% of the molecular iodine was lost in the sample that contained carboxymethylcellulose. More than 30% of the molecular iodine was lost in the sample that contained hydroxyproplymethylcellulose. The sample containing 5% Poloxamer-188 exhibited a reduction in the concentration of molecular iodine of 10% by hour 6 and over 25% in 24 hours. In contrast to the other polymers, Carbopol Ultrez 30 was compatible with molecular iodine for more than 9 months. Although there was an initial reduction in the absolute concentration of molecular iodine of about 25% the loss stabilized and this polymer can be combined with molecular iodine for an extended time period.

Example 4

Alpha cyclodextrin, beta cyclodextrin, gamma cyclodextrin (γ-cyclodextrin, cat. number C4892, Sigma Life Sciences, Lot SLBL4156V, CAS 17465-86-0), methyl beta cyclodextri, and 2-hydroxypropyl-beta-cyclodextrin The following cyclodextrins were tested for compatibility with molecular iodine: α- (cat. number C4642, Sigma Life Sciences, Lot 2X SLBK4630V, CAS 10016-20-3), β- (cat. number C4767, Sigma Life Sciences, Lot MKBV2085V, CAS 7585-39-9), γ- (cat. number C4892, Sigma Life Sciences, Lot SLBL4156V, CAS 17465-86-0), methyl-β- (cat. number C4555, Sigma Life Sciences, Lot WXBC0745V, CAS 128446-36-6), and hydroxypropyl-β-cyclodextrin (H107, Sigma Life Sciences, Lot WXBC0083V, CAS 128446-35-5).

Solutions of these cyclodextrins were prepared in acetate buffer or propylene glycol, both containing molecular iodine as follows. Cyclodextrins were weighed and added to vials. Saturated solutions of molecular iodine (Alfa Aesar 14248 Lot 104Z003) were then prepared in either: (a) 30 mM acetate buffer (pH 4.5); or (b) propylene glycol. The measured concentrations of iodine in these solutions were 112 and 672 ppm, respectively.

Aliquots of each solution of the different cyclodextrins were added to vials to a final cyclodextrin concentration of 50 mM. Control vials that contained only saturated solutions of molecular iodine in acetate buffer or propylene glycol were also prepared. The screw-top lid of each vial was fitted with an iodine sensitive paper disc (Fluka #37215, Lot SZBF1310V) that fit tightly in the lid so the paper was exposed to the atmosphere in the vial which would allow the paper to react with molecular iodine that was in the vapor phase.

Figure 1B:
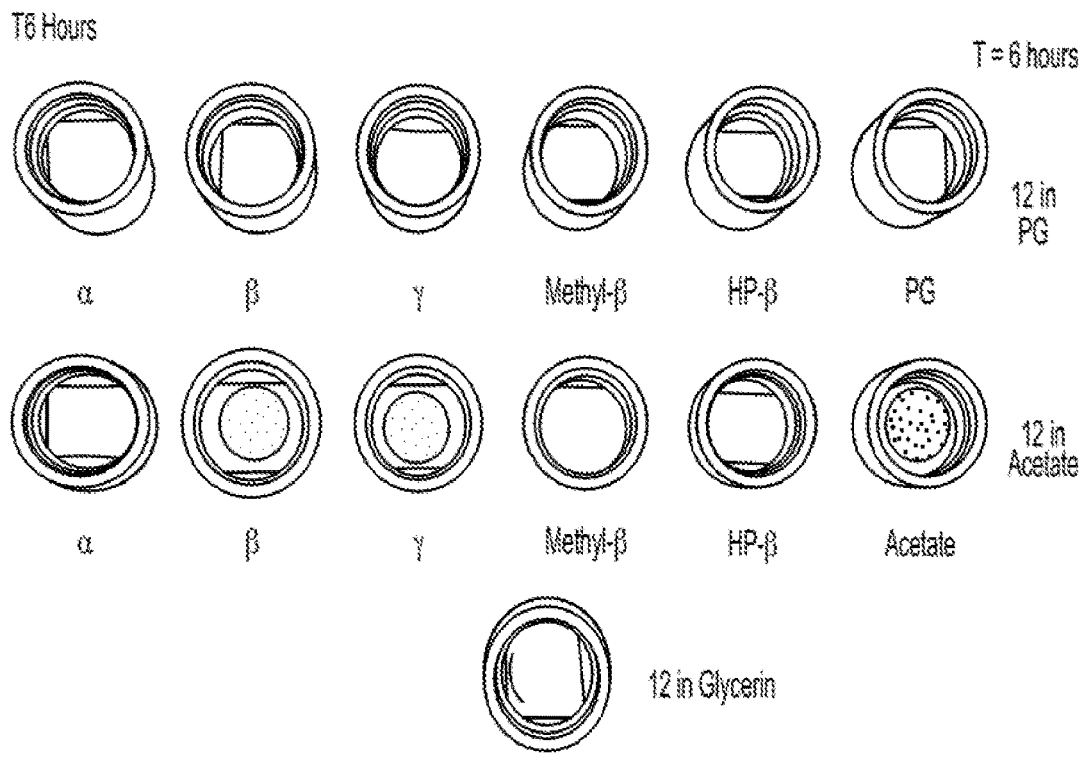

At time points of: one (1) hour; six (6) hours; and twenty-four (24) hours, the color of the indicator paper on the inside of the screw-top lids were examined and photographed. These results are shown in FIGS. 1A-1C.

At 1 hour the control sample of molecular iodine in acetate buffer was highly colored. At 6 hours, the same control sample was almost 100% black. The only change observed at 24 hours was a discoloration of the paper, which was probably partially protected by the threads of the screw-top vial.

At 1 hour there was little or no color on any of the cyclodextrin samples prepared in acetate buffer. At 6 hours the molecular iodine vapor was clearly detected in the samples of beta and gamma cyclodextrin. At 24 hours molecular iodine vapor was clearly detected in the hyroxypropyl-β-cyclodextrin sample and the indicator paper in the samples of samples of beta and gamma cyclodextrin were deeply stained.

At 1 hour and 6 hours there was little or no color on the cyclodextrin samples prepared in propylene glycol. At 24 hours molecular iodine vapor could be detected on the indicator paper in all of the cyclodextrin samples prepared in propylene glycol; however, the intensity of the color in the propylene glycol samples was substantially less than the acetate samples.

The data observed indicates that α-cyclodextrin, methyl-β-cyclodextrin, and hyroxypropyl-β-cyclodextrin reduces the vapor pressure of molecular iodine in an aqueous environment. Accordingly, these agents can be used to stabilize an aqueous composition of molecular iodine.

Molecular iodine in propylene glycol and molecular iodine acetate buffer served as controls in this experiment; a comparison of the indicator paper in these two control samples establishes the ability of propylene glycol to reduce the vapor pressure of molecular iodine.

A comparison of the intensity of the indicator paper from these two samples indicates that propylene glycol can reduce the vapor pressure of molecular iodine by at least two orders of magnitude.

An additional control of molecular iodine in glycerol (1,120 ppm) was also included in this experiment. The color intensity of the indicator paper for molecular iodine in glycerol was visually indistinguishable from that observed for propylene glycol.

Example 5

Alpha cyclodextrin (cat. number C4642, Sigma Life Sciences, Lot 2X SLBK4630V, CAS 10016-20-3), beta cyclodextrin (cat. number C4767, Sigma Life Sciences, Lot MKBV2085V, CAS 7585-39-9), gamma cyclodextrin (cat. number C4892, Sigma Life Sciences, Lot SLBL4156V, CAS 17465-86-0), methyl beta cyclodextri, (cat. number C4555, Sigma Life Sciences, Lot WXBC0745V, CAS 128446-36-6) and 2-hydroxypropyl-beta-cyclodextrin (cat. number H107, Sigma Life Sciences, Lot WXBC0083V, CAS 128446-35-5) were weighed into vials.

Aliquots of saturated molecular iodine in either propylene glycol or 0.1M acetate buffer (pH 4.5) were added to the vials to yield a final cyclodextrin concentration of 50 mM. The samples were lightly vortexed to dissolve the cyclodextrins. Control vials were prepared consisting of saturated iodine in either propylene glycol or 0.1M acetate buffer pH 4.5.

A saturated solution of molecular iodine in glycerin was also prepared and included in this experiment. Analytical potassium iodide starch paper (Fluka #37215, Lot SZBF1310V) was cut into circle and placed inside the screw-top lid of the vials in a manner that held the paper in place once the lid was screwed onto the vial.

Provided in FIGS. 2A-2L are pictures of the starch paper taken at different time points to document the color of the starch paper versus time of exposure to the atmosphere inside of the vial. The operating assumption was that the color of the starch paper would be proportional to the time of exposure to the concentration of molecular iodine in the atmosphere inside of the vial.

The concentration of molecular iodine in the atmosphere inside of the vial is proportional to the vapor pressure of dissolved molecular iodine in the liquid phase. The vapor pressure of molecular iodine in pure acetate buffer was expected to be higher than all other experimental conditions, i.e. the starch paper in the acetate vial was expected to turn color more rapidly than the other experimental treatments. The data demonstrated this to be correct.

Starch paper coloration of the acetate only vial is detectable to the eye as early as 5 minutes and continues increasing until 4 hours at which point the reagents in the starch paper were fully spent.

Notably, the starch paper coloration of the glycerin control and the propylene glycol control experiment vials at 48 hours are less than or equal to the coloration in the acetate control vail at 20 minutes. In other words, the "effective" relative vapor pressure of molecular iodine in these two solvents is about two orders of magnitude lower than that in water.

The cyclodextrins appeared to lower the vapor pressure of molecular iodine in an aqueous environment, i.e. acetate buffer, as evidenced by the lower color intensity of the cyclodextrin vials as compared to the acetate control. However, some cyclodextrins were more effective in reducing the vapor pressure of molecular iodine. For example, α-cyclodextrin, methyl-β-cyclodextrin, and hyroxypropyl-β-cyclodextrin provided the greatest reduction in vapor pressure of molecular iodine in the acetate buffer. Unexpectedly, of these three cyclodextrins, only α-cyclodextrin and methyl-β-cyclodextrin reduced the vapor pressure of molecular iodine by 2 orders or magnitude or more.

The concentration of molecular iodine was measured by titration at the beginning and end of these experiments to determine if the reduction in starch paper color intensity was due to a cyclodextrin-induced reduction of molecular iodine to iodide. Over 65% of the initially measured molecular iodine at time 0 was present at time 48 hours for all of the cyclodextrins except γ-cyclodextrin.

This was a remarkably high concentration of the initial molecular iodine since simply opening and closing the control vial results in the loss of about 70% of the molecular iodine in the acetate control vial. These observations demonstrated that α-cyclodextrin, β-cyclodextrin, methyl-β-cyclodextrin, and hyroxypropyl-β-cyclodextrin can serve to reduce the vapor pressure of molecular iodine in an aqueous environment, with α-cyclodextrin, methyl-β-cyclodextrin and hyroxypropyl-β cyclodextrin being particularly effective and methyl-β-cyclodextrin and hyroxypropyl-β cyclodextrin being the most effective.

A similar cyclodextrin-induced vapor pressure reduction was not observed in propylene glycol which may be attributable to a different partition coefficient for molecular iodine in water versus propylene glycol. To demonstrate how effective both glycerin and propylene glycol are in stabilizing molecular iodine the level of molecular iodine was measured by titration at the start and end of these experiments. The percentage of original molecular iodine detected in the glycerin sample at 48 hours was 96.6% and the value for propylene glycol was 94.5% despite opening and closing the vial lid multiple times.

Example 6

Molecular iodine was dissolved in glycerin and propylene glycol and then tested to determine if molecular iodine dissolved in these organic carriers is available to inactivate a methicillin-resistant (MRSA) Staphylococcus aureus strain (MRSA TCH1516).

Viable MRSA TCH1516 were washed, spun down, resuspended and 200 µL of the bacteria was streaked onto Standard Methods agar plates (Cole Palmer, Vernon Hills, Ill.; Item #EW-14201-44). The lid on the plates was removed and the plates were placed in a 37° C. incubator with the bottom of the plate on top to remove any residual moisture from the surface of the plate. Plates were maintained in this position for over an hour to "dry" the surface of the bacterial lawn.

Plates were then removed from the incubator and 20 µL of a carrier with molecular iodine was applied to the lawn. The lid was replaced on the agar plates and the plates were returned to the incubator to grown until a thick lawn of bacteria was present.

Figure 3A:
FIGS. 3A and 3B illustrate the results from Example 6, according to one embodiment of the invention.

As shown in FIG. 3A, the plate that received propylene glycol carrier had a clear circle in its center where the 20 µL of propylene glycol with 952 ppm molecular iodine was deposited. The size of the circle was significantly greater than the surface area covered by a 20 µL fluid volume indicating that there was some diffusion. The biocidal capability of this composition was clearly demonstrated.

Figure 3B:
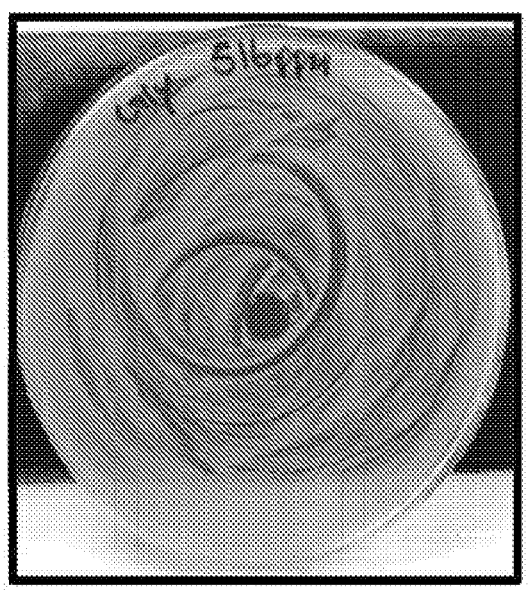

Equivalent results were observed with the glycerin-iodine sample. As illustrated in FIG. 3B, the area of bacterial killing in the case of glycerin was less than that observed with the propylene glycol sample but the concentration of molecular iodine (516 ppm) in the glycerin sample was about half of that in the propylene glycol carrier.

Both of these examples demonstrate the ability of molecular iodine to inactivate pathogens when incorporated in the preferred organic carriers identified in this application.

Example 7

The rheological properties of a composition intended for use as a nasal topical is an important formulation consideration. Once an antimicrobial is placed in a nasal cavity its residence time can influence its ability to eliminate microbes present in the nasal cavity. Consequently, the present invention contemplates composition of matter that incorporates viscosity enhancing agents.

Fluid viscosity is essentially the transfer of momentum that results from collisions with other molecules. When thought of in this manner it's not surprising that fluids exhibit different viscosities when placed in different states; ketchup is the one example all people are familiar as its apparent viscosity required to initial flow is higher than that one flow has progressed.

Figure 4A:
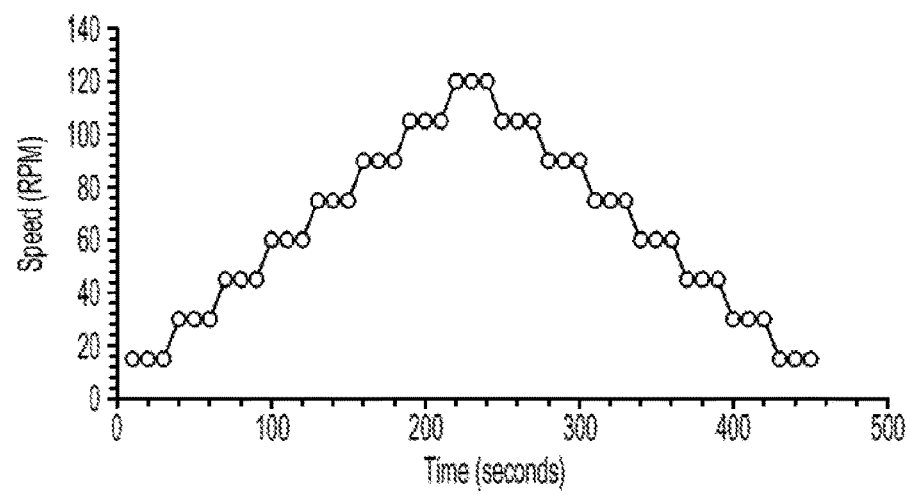

Viscosity was measured using a Brookfield DV2T viscometer which allowed for the precise control of the temperature at which the viscosity was measured. The Brookfield DV2T was programmed to measured viscosity at different shear rates by systematically ramping the spindle (CP-40 or CP-52) speed up and then down as shown in FIG. 4A for propylene glycol at 25° C.

Figure 4B:
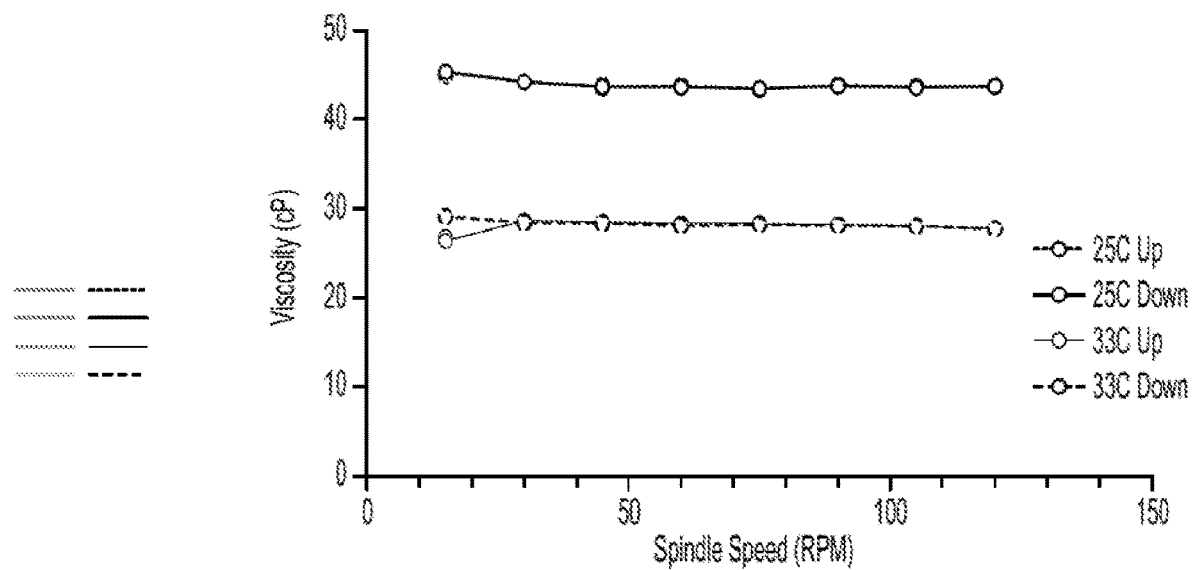

The viscosity measurements at each spindle speed were then plotted as shown in FIG. 4B. Propylene glycol behaves like a Newtonian fluid as the viscosity is largely independent of the shear and identical for increasing and decreasing shear. The viscosity values were fitted to a curve and extrapolated to the zero shear value to arrive at a final estimate for viscosity.

The viscosity of propylene glycol at 25° C. and 33° C. was calculated to be 59 centipoise (cP) and 95 cP (centipoise). A temperature of 33° C. was selected as a representative thermal environment on the lining of the nasal cavity. The viscosity of an existing commercial product (3M™ Skin and Nasal Antiseptic; Povidone-Iodine Solution 5% w/w [0.5% available iodine] USP) Patient Preoperative Skin Preparation, Catalog item 192401) was selected for use as a viscosity control. The viscosity of the 3M™ Skin and Nasal Antiseptic product was measured at 25° C. and 33° C. The results of which are shown in Table 1 below.

TABLE 1

Viscosity of 3M ™ Skin and Nasal Antiseptic

| Brookfield Cone # | Temperature ° C. | Viscosity (cP) | Date of Measurement |
|---|---|---|---|
| CP-40 | 25 | 5100 | 11 MAR. 2016 |
| CP-40 | 33 | 3788 | 11 MAR. 2016 |
| CP-40 | 25 | 4907 | 15 MAR. 2016 |
| CP-40 | 33 | 3565 | 15 MAR. 2016 |

Several compositions of propylene glycol that contained Carbopol Ultrez 30 polymer (Lubrizol Company, Cleveland, Ohio) in propylene glycol were prepared with increasing concentrations of 0.1%, 0.2%, 0.3%, 0.4% and 0.5% of Ultrez 30 in PG.

One series of samples was prepared without molecular iodine and a second series was prepared that contained 800 ppm molecular iodine. The viscosity of these samples was measured as described above using an up-down rate ramp program. The results were fitted to an Ostwald model, i.e. stress versus shear rate curve fit, and the consistency constant was reported as the viscosity. The basic data demonstrated non-Newtonian viscosity for the Ultrez 30 samples. The results showed a step increase in viscosity with increasing Ultrez 30 concentration. Unexpectedly, as illustrated in FIG. 4C, the Ultrez 30 viscosity profile differed for samples with or without iodine.

As illustrated in Table 2 below, the data demonstrated that Carbopol Ultrez 30 can be used to prepare formulations that provide a wide range viscosity suitable for topical applications in the nasal cavity as well of other mammalian surfaces.

TABLE 2

| Sample | Temperature ° C. | Viscosity |
|---|---|---|
| 0.1% Carbopol Ultrez 30 in PG | 33 | 59.9 |
| 0.2% Carbopol Ultrez 30 in PG | 25 | 487 |
| 0.2% Carbopol Ultrez 30 in PG | 33 | 374 |
| 0.3% Carbopol Ultrez 30 in PG | 25 | 1082 |
| 0.3% Carbopol Ultrez 30 in PG | 33 | 1137 |
| 0.4% Carbopol Ultrez 30 in PG | 25 | 5123 |
| 0.4% Carbopol Ultrez 30 in PG | 33 | 4996 |

TABLE 2-continued

| Sample | Temperature ° C. | Viscosity |
|---|---|---|
| 0.5% Carbopol Ultrez 30 in PG1 | 25 | 13370 |
| 0.5% Carbopol Ultrez 30 in PG1 | 33 | 11197 |
| 1% Carbopol Ultrez 30 in PG | 25 | 80012 |
| 1% Carbopol Ultrez 30 in PG | 33 | 68963 |

Example 8

Healthy 10-12-week-old Hsd:ICR mice weighing 25-30 grams (Females) or 30-35 grams (Males) were housed in cages containing five animals and provided with mouse chow and water available ad libitum. The animals were arbitrarily assigned to one of three treatment regimens. All mice in a single cage were assigned to the same treatment regimen. The treatment regimens were: (a) glycerin (negative control); (b) 3M™ Skin and Nasal disinfectant; and (c) 400 ppm molecular iodine in glycerin. The experiment was repeated three separate days.

Mice were challenged with a suspension containing 10E8 CFU/mL of MRSA TCH1516 pipetted (10 µL) into each naris. Twenty-four hours later one of the three treatments described above was applied to the naris (10 µL) of each of the mice. Twenty-four hours after applying the treatment to the mice the mice were euthanized and their nasal cavity was isolated. The nasal cavities were vortexed vigorously (10 seconds, times 3) in phosphate-buffered saline (PBS), serial dilutions were made in PBS and plated in triplicate onto Todd Hewitt agar (THA) plates. The plates were incubated in room air at 37° C. for 12 h.

The triplicate plate counts were performed on a total of 25 mice in each the treatment groups for a total of 75 averaged values. Out of the 25 animals in the control arm, a total of 6 mice exhibited a very low colonization (CFU/nasal cavity<1,500). The average CFU/nasal cavity in the remaining 19 animals in the control group was 11,051. Both the 3M™ Skin and Nasal disinfectant and the molecular iodine-glycerin treatment significantly reduced MRSA in the nasal cavity. The mean MRSA reduction with the 3M product was 2.15 logs as compared to 2.40 logs with molecular iodine.

Clinical success in a patient in this application is more accurately evaluated using binomial statistics since an average reduction does not incorporate an evaluation of the proportion of individual patients who benefited. Therefore, in order to be considered a treatment success a minimum two-log reduction criterion was applied. Using this more appropriate criterion the 3M product exhibited 9 failures in 25 mice as compared to only 3 failures with molecular iodine. This demonstrates a statistically significant difference between the 3M product and the molecular iodine product described herein.

What is claimed is:
1. An emollient antimicrobial composition comprising:
   (a) an organic carrier molecule selected from the group consisting of propylene glycol, glycerol, and a combination thereof; and
   (b) molecular iodine; and
   the ratio of molecular iodine to all iodine species being at least about 70%; and
   the vapor pressure of molecular iodine in the emollient antimicrobial composition being at least two magnitude lower than the vapor pressure of molecular iodine in water.

2. The emollient antimicrobial composition of claim 1, the concentration of molecular iodine being between about 10 ppm and about 1000 ppm.

3. The emollient antimicrobial composition of claim 1, wherein the ratio of molecular iodine to all iodine species is at least about 90%.

4. The emollient antimicrobial composition of claim 1, wherein the composition further comprises one or more gelling agents selected from the group consisting of homopolymers of acrylic acid, homopolymers of methyl glucoside derivatives, homopolymers of alcohol esters, polyethylehe glycols (PEG), carrageenan, locust bean gum, guar gum, acacia, tragacanth, alginic acid, gelatin, carboxymethyl cellulose, methyl cellulose, and hydroxypropyl methyl cellulose.

5. The emollient antimicrobial composition of claim 1, wherein the viscosity is between 500 and 10,000 centipoise.

6. The emollient antimicrobial composition of claim 1, wherein the composition further comprises one or more organic molecules selected from the group consisting of monomethyl ether, acetate, amyl alcohol, ethyl acetate, butyl acetate, dimethylsulfoxide, 1-propanol, 2-propanol, dimethyl sulfoxide, iso-propanol, and ethanol.

7. The emollient antimicrobial composition of claim 1, further comprising a saturated fatty acid selected from the group consisting of lactic acid, myristic acid, 1-monolaurin, dodeconic acid, and caprylic acid.

8. The emollient antimicrobial composition of claim 1 formulated for a dermal application.

9. The emollient antimicrobial composition of claim 8, wherein the dermal application is in the form of a hand sanitizer, a cream, foam, gel, lotion, or ointment dosage form.

10. The emollient antimicrobial composition of claim 1 formulated for nasal application.

11. The emollient antimicrobial composition of claim 10, wherein the nasal application is a spray dosage form, wherein the spray dosage form is in the form of a metered dose inhaler.

12. A method for treating a bacterial infection comprising administering a therapeutically effective amount of the emollient antimicrobial composition of claim 1.

13. A method for treating a hospital acquired infection comprising administering an effective amount of the emollient antimicrobial composition of claim 1.

14. The method of claim 13, wherein the hospital acquired infection is Staphylococcus aureus, Pseudomonas aeruginosa, Acinetobacter baumannii and Enterobacteriaceae including E. coli, Klebsiella pneumoniae, Shigella or Yersinia.

* * * * *